(12) United States Patent
Mikkaichi et al.

(10) Patent No.: US 8,702,753 B2
(45) Date of Patent: Apr. 22, 2014

(54) METHOD FOR SUTURING PERFORATION AND SUTURE INSTRUMENT

(75) Inventors: Takayasu Mikkaichi, Tokyo (JP); Kunihide Kaji, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1240 days.

(21) Appl. No.: 11/238,006

(22) Filed: Sep. 28, 2005

(65) Prior Publication Data
US 2007/0073319 A1 Mar. 29, 2007

(51) Int. Cl.
*A61B 17/04* (2006.01)
(52) U.S. Cl.
USPC .............................. 606/232; 606/139; 606/144
(58) Field of Classification Search
CPC ............. A61B 17/08; A61B 17/0482; A61B 17/0485; A61B 17/0401
USPC ........................................ 606/139, 144, 232
See application file for complete search history.

(56) References Cited

U.S. PATENT DOCUMENTS

| | | | | |
|---|---|---|---|---|
| 3,875,648 A * | 4/1975 | Bone | ................................ | 29/417 |
| 4,006,747 A * | 2/1977 | Kronenthal et al. | ........... | 606/144 |
| 4,235,238 A * | 11/1980 | Ogiu et al. | ..................... | 606/145 |
| 4,696,300 A * | 9/1987 | Anderson | ..................... | 606/219 |
| 4,950,285 A | 8/1990 | Wilk | | |
| 5,021,059 A * | 6/1991 | Kensey et al. | .................. | 606/213 |
| 5,041,129 A * | 8/1991 | Hayhurst et al. | .............. | 606/232 |
| 5,269,809 A * | 12/1993 | Hayhurst et al. | .............. | 606/232 |
| 5,470,337 A * | 11/1995 | Moss | .............................. | 606/139 |
| 5,593,422 A * | 1/1997 | Muijs Van de Moer et al. | ............................. | 606/213 |
| 5,593,424 A * | 1/1997 | Northrup, III | ................. | 606/232 |
| 5,810,848 A * | 9/1998 | Hayhurst | ....................... | 606/144 |
| 6,071,292 A * | 6/2000 | Makower et al. | .............. | 606/158 |
| 6,287,317 B1 * | 9/2001 | Makower et al. | .............. | 606/153 |
| 6,290,674 B1 * | 9/2001 | Roue et al. | ..................... | 604/107 |
| 6,319,271 B1 * | 11/2001 | Schwartz et al. | .............. | 606/232 |
| 6,491,707 B2 * | 12/2002 | Makower et al. | .............. | 606/157 |
| 6,500,184 B1 * | 12/2002 | Chan et al. | ..................... | 606/144 |
| 6,635,073 B2 * | 10/2003 | Bonutti | ......................... | 606/232 |
| 6,641,557 B1 * | 11/2003 | Frazier et al. | .................. | 604/115 |
| 7,087,073 B2 * | 8/2006 | Bonutti | ......................... | 606/232 |
| 7,534,248 B2 * | 5/2009 | Mikkaichi et al. | ............. | 606/144 |
| 2003/0105474 A1 | 6/2003 | Bonutti | | |
| 2004/0249392 A1 * | 12/2004 | Mikkaichi et al. | ............. | 606/142 |
| 2005/0149067 A1 | 7/2005 | Takemoto et al. | | |

FOREIGN PATENT DOCUMENTS

| | | |
|---|---|---|
| CA | 2 306 528 A1 | 12/1996 |
| EP | 1 484 023 A1 | 12/2004 |
| EP | 1 584 294 A2 | 10/2005 |
| JP | 2003-225241 | 8/2003 |
| JP | 2003-299661 | 10/2003 |
| JP | 2004-358046 | 12/2004 |

OTHER PUBLICATIONS

Japanese Office Action dated Feb. 23, 2010 with translation.
Japanese Official Action dated Aug. 31, 2010 together with an English language translation.

* cited by examiner

*Primary Examiner* — Melanie Tyson
*Assistant Examiner* — Katelyn Bernier
(74) *Attorney, Agent, or Firm* — Scully, Scott, Murphy & Presser, P.C.

(57) ABSTRACT

A method for suturing a perforation formed in a hollow organ comprises the steps of:
  causing plural end portions of the suture thread to puncture a tissue around the perforation in the same direction as each other;
  connecting the end portions of the suture thread to each other; and
  tightening up the suture thread after connecting the end portions of the suture thread with each other.

7 Claims, 16 Drawing Sheets

METHOD FOR SUTURING PERFORATION AND SUTURE INSTRUMENT

BACKGROUND OF THE INVENTION

1. Field of the Invention

This invention relates to a suturing method using an endoscope and a suture instrument used for suturing. For example, this invention relates to a method for suturing a perforation formed in a wall of a hollow organ and a suture instrument used therefore.

2. Description of Related Art

In the case of performing treatment in a body of a patient, the treatment can be performed by incising the body of the patient by surgical operation, or by oral endoscopic treatment or transanal endoscopic treatment. In the case of using an endoscope, the treatment can be performed by passing through a channel of the endoscope a forceps, high-frequency treatment instrument, incision instrument, suture instrument, or the like. In the case of using an endoscope inserted in the lumen from natural opening of a living body such as, for example, the mouth or anus to perform a medical treatment in the abdominal cavity, tissue is removed from the abdominal cavity or incised to form a hole, and then the medical treatment is carried out by approaching the abdominal cavity from the lumen through this hole. After the end of the medical treatment, the formed hole is sutured by using a suture instrument.

As a method for suturing a perforation formed in a hollow organ, a suturing method is disclosed in FIGS. 12 to 15 of U.S. Pat. No. 6,290,674. In this suturing method, a catheter for closing the interatrial septum is used. At the tip of the catheter, an anchor supporting member containing an anchor is provided. The anchor supporting member projects through a perforation from the inside to the outside of the tissue. From the anchor supporting member, two anchors are respectively made to perforate the tissue from the outside to the inside thereof. After that, the anchor supporting member is drawn out from the perforation. Since a suture thread is fixed to the anchor, the suture thread penetrates the tissue from the inside to the outside thereof. The suture thread is drawn from the outside into the inside of the tissue through the perforation. When the suture thread is tightened up, the tissue around the perforation is pulled together, and thereby the perforation is closed.

SUMMARY OF THE INVENTION

A method for suturing a perforation of the present invention comprises the steps of:

causing plural end portions of the suture thread to puncture a tissue around the perforation in the same direction as each other;

connecting the end portions of the suture thread to each other; and tightening up the suture thread after connecting the end portions of the suture thread with each other.

DETAILED DESCRIPTION OF THE INVENTION (First Embodiment)

Figure 1:
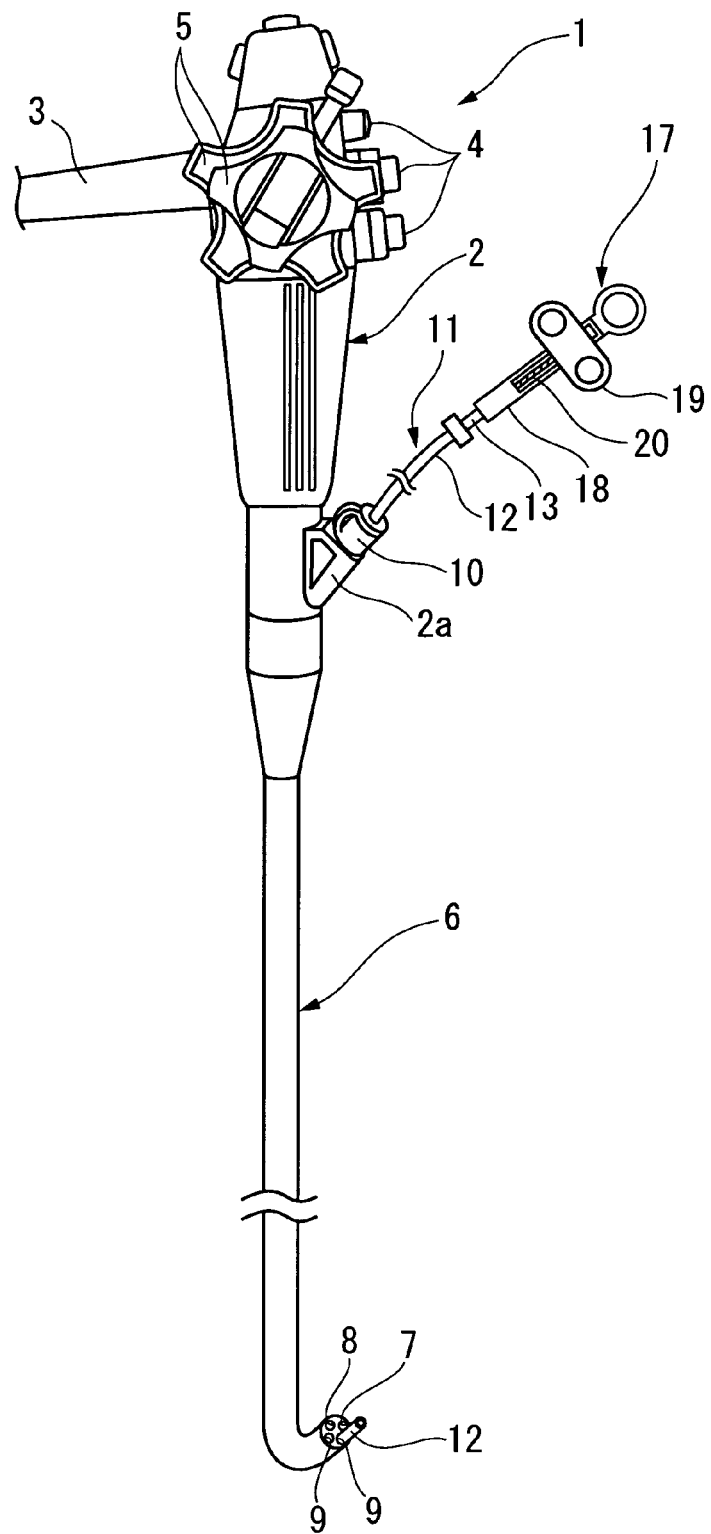
FIG. 1 is a view showing a schematic constitution of an endoscope and a suture unit.

In FIG. 1, an endoscope and a suture unit used in this embodiment are shown. An endoscope 1 (flexible endoscope) has an endoscope operation unit 2 which is operated by an operator. The endoscope operation unit 2 is connected to a control device via a universal cable 3 and equipped with various switches 4 and angle knobs 5. At the tip of the endoscope operation unit 2, an endoscope insertion part 6 that is flexible and long is extendedly formed. At the tip of the endoscope insertion part 6, an observation device 7 for obtaining an image of the internal body, a lighting unit 8, and a tip opening of a channel 9 are provided. As the observation device 7, an imaging device having a CCD (Charge Coupled Device) or an optical fiber can be used. The lighting unit 8 has an optical fiber that conducts light from a light source. The channel 9 opens at a lateral part 2a of the endoscope operation unit 2 through the endoscope insertion part 6. At an opening of the lateral part 2a, a cap 10 is provided. In the cap 10, an insertion hole is formed, and a treatment instrument such as a suture unit 11 is inserted into the channel 9 through this insertion hole.

Figure 2:
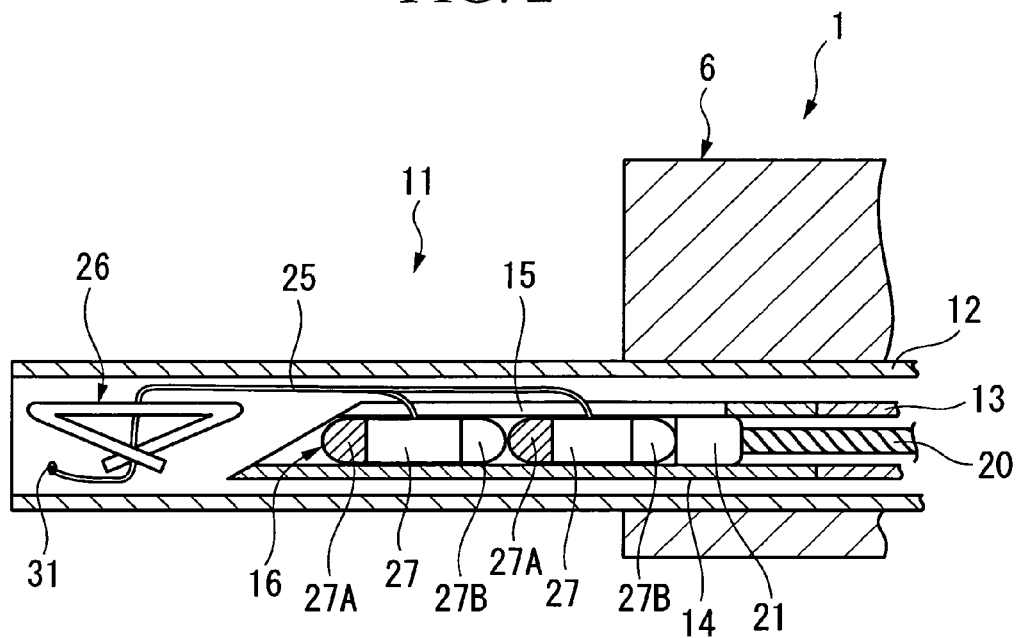
FIG. 2 is a cross-sectional view of a suture unit and an end portion of an endoscope.
Figure 3:
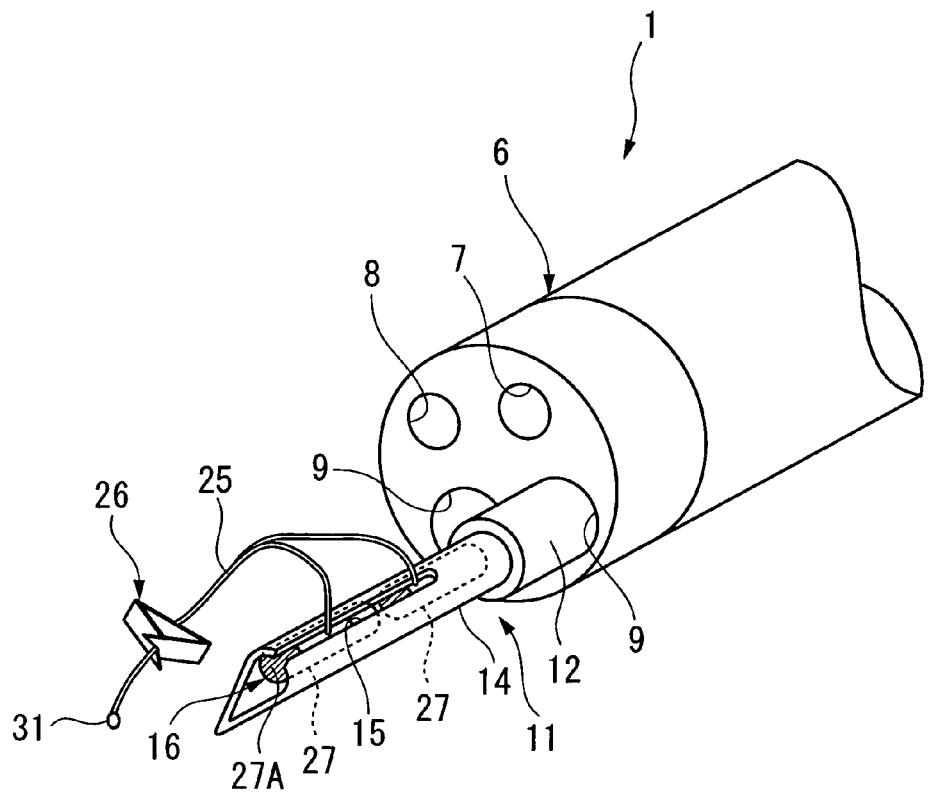
FIG. 3 is a perspective view of a suture unit and an end portion of an endoscope.

As shown in FIGS. 1 to 3, in the suture unit 11, a flexible inner sheath 13 is passed through the inside of a flexible outer sheath 12 so as to be able to freely move. To the tip of the inner sheath 13, a needle 14 is fixed. The needle 14 has a slit 15 formed in a longitudinal direction from the tip thereof. A suture instrument 16 is contained inside of the needle 14. Each of the lengths of the outer sheath 12 and the inner sheath 13 is longer than that of the channel 9 of the endoscope 1. At a proximal end of the inner sheath 13, an operation unit 17 is provided. The operation unit 17 has a handle 19 which can freely slide with respect to a main body 18 of the operation unit. To the handle 19, a proximal end of a pusher 20 is fixed. The pusher 20 extends through the inside of the inner sheath 13 to the inside of the needle 14. A distal end portion 21 of the pusher 20 is pressed against the suture instrument 16.

Figure 4:
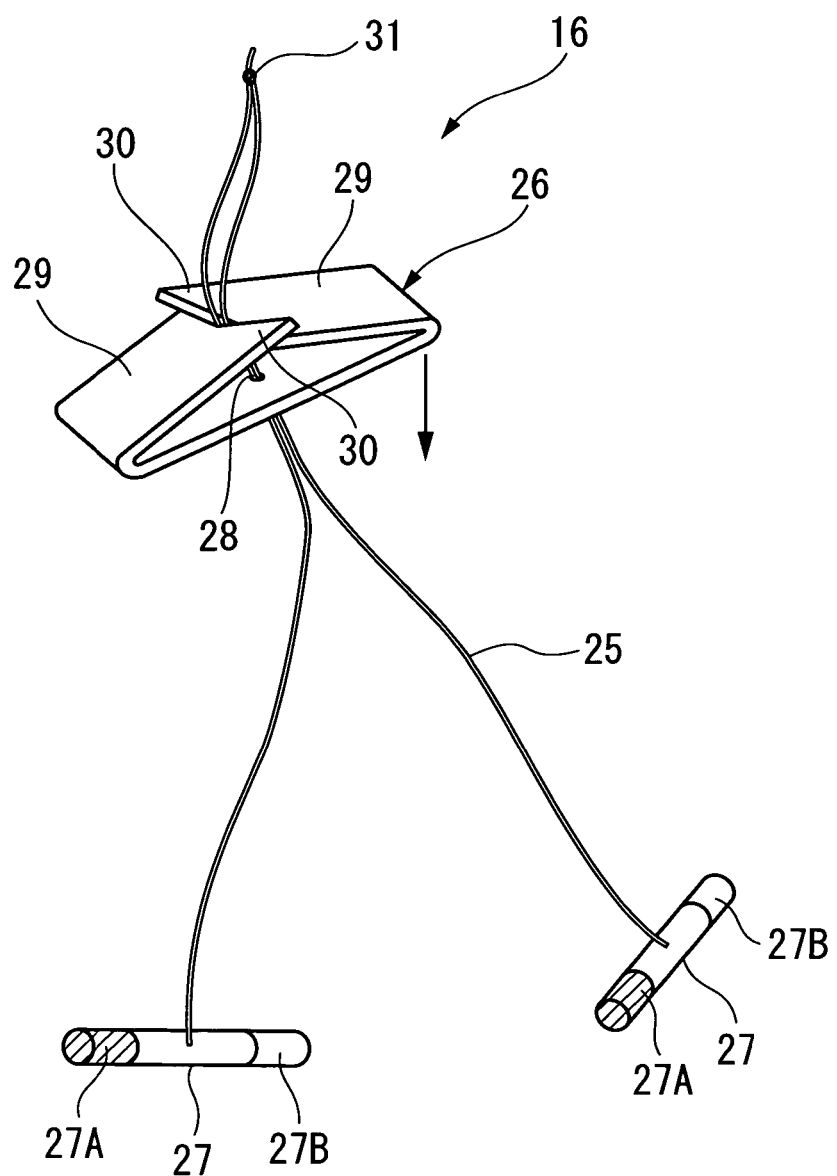
FIG. 4 is a view showing a constitution of a suture instrument.

As shown in FIG. 4, the suture instrument 16 has a suture thread 25. The suture thread 25 is folded approximately in two and a knot 31 is formed in the vicinity of its turn-around point. Moreover, the suture thread 25 is bundled at both end portions (a first end portion and a second end portion) thereof and passed through a stopper 26 that is substantially triangular. To each of the first end portion and the second end portion of the suture thread 25, an anchor 27 is fixed. The anchor 27 has a cylindrical shape and the suture thread 25 is fixed at an approximately center portion in a longitudinal direction of the anchor 27. Both end portions of two anchors 27 in their longitudinal direction are respectively polarized. One end portion 27A of the anchor 27 becomes a south pole of a magnet, and the other end portion 27B becomes a north pole of the magnet. In FIG. 4, the end portion 27A of the south pole and the end portion 27B of the north pole are distinguished by using different colors so as to allow visual distinction. However, the end portions 27A and 27B and other portions may not be distinguished by using different colors.

The stopper 26 includes a long, thin plate member in which a hole 28 is formed at the center portion in a longitudinal direction thereof, through which the suture thread 25 is passed. Both end portions 29 in a longitudinal direction of the stopper 26 are diagonally folded back to hold the suture thread 25 therebetween. Both end portions 29 in a longitudinal direction of the stopper 26 are cut to form triangular sections 30. Both end portions 29 of the stopper 26 are diagonally folded back so that the sections 30 intersect with each other to hold the suture thread 25 therebetween. As a result, the suture thread 25 is prevented from passing through a space formed between end portions 29. When the knot 31 of the suture thread 25 is pulled in a direction away from the stopper 26, both end portions 29 of the stopper 26 are slightly opened. Accordingly, the stopper 26 allows the suture thread 26 to move in the same direction. On the other hand, when end portions of the suture thread 25 at the side of the anchors 27 are pulled, the suture thread 25 is ready to move in a direction shown by an arrow in FIG. 4. At this time, however, the suture thread 25 does not move, since both end portions 29 of the stopper 26 are closed and secure the suture thread 25.

As shown in FIG. 3, the suture instrument 16 sequentially holds two anchors 27 in an inner hole of the needle 14. The suture thread 25 is drawn out from the slit 15 of the needle 14. As shown in FIG. 2, the stopper 26 is held at a more distal end portion than the needle 14 in the outer sheath 12. The number of the anchors 27 and the shape of the stopper 26 are not limited to the embodiment shown in the figures.

Next, a suturing method of this embodiment will be explained mainly with reference to FIGS. 5 to 14. FIGS. 5 to 12 are pattern diagrams illustrating manipulation and show the stomach as an example of a hollow organ.

Figure 5:
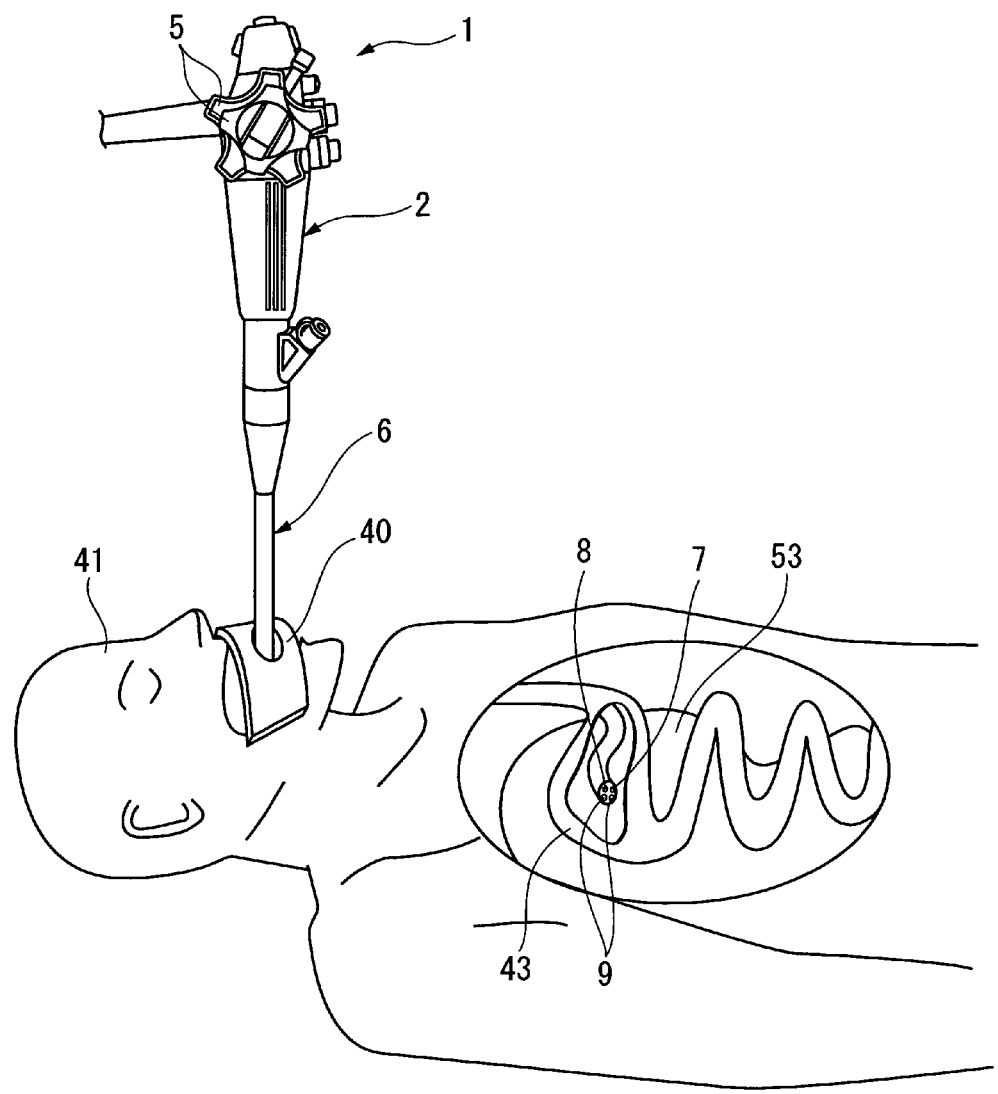
FIG. 5 is a view showing a step of inserting an endoscope into the stomach of a patient to observe a proposed incision position from the inside of the stomach.
Figure 6:
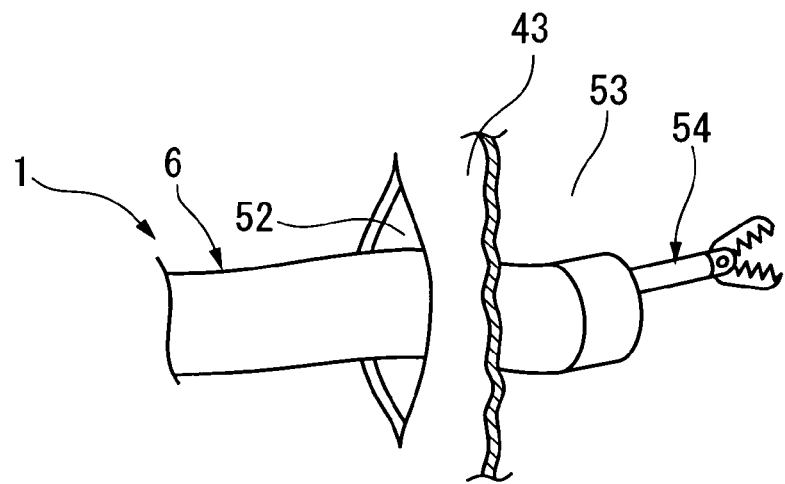
FIG. 6 is a view showing a step of inserting an endoscope insertion part from a perforation into the abdominal cavity to carry out treatment.

As shown in FIG. 5, the endoscope insertion part 6 is inserted from the mouth (a natural opening of a living body, such as the anus, nose, or ear) of a patient 41 prepared with a mouthpiece 40. The tip of the endoscope insertion part 6 is bent by the angle knob 5. A needle-like knife that is a high-frequency incision tool is passed through the channel 9 of the endoscope insertion part 6, and a perforation is formed by incising the tissue of the wall of the stomach 43. As shown in FIG. 6, the endoscope insertion part 6 is directed to the abdominal cavity 53 through the perforation 52 formed in the stomach 43. A forceps 54 is passed through the channel 9, and the treatment in the abdominal cavity 53 is carried out by using the forceps 54. After finishing the treatment, the endoscope insertion part 6 is drawn back to the inside of the stomach 43.

Figure 7:
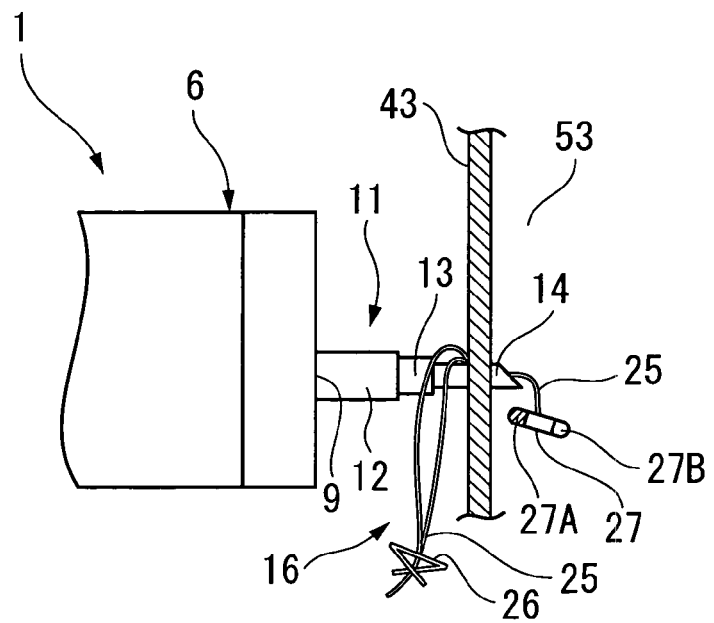
FIG. 7 is a view showing a step of thrusting a needle to extrude an anchor into an abdominal cavity side.
Figure 8:
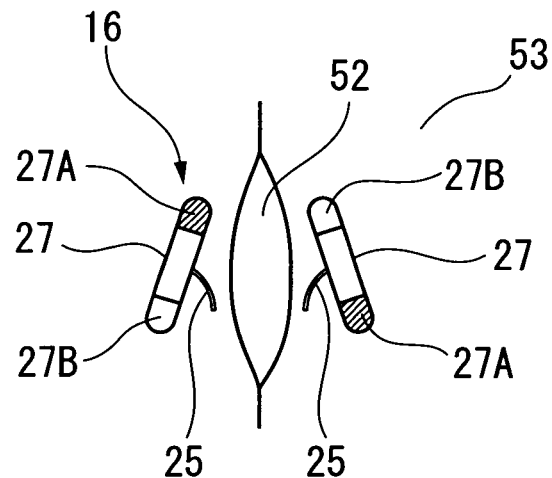
FIG. 8 is a view indicating the state as viewed from an abdominal cavity side, in which an anchor is placed.

When the perforation 52 is sutured, the suture unit 11 is passed through the channel 9 of the endoscope insertion part 6, and the needle 14 of the suture unit 11 is projected from the outer sheath 12. At this time, the stopper 26 falls to the stomach 43. When the suture unit 11 is moved forward, the needle 14 is thrust into the tissue around the perforation 52 (inside of the stomach 43). When the tip portion of the needle 14 penetrates the tissue and projects to the abdominal cavity 53 side, the forward movement of the suture unit 11 is stopped. The handle 19 (see FIG. 1) of the operation unit 17 is manipulated to move the pusher 20 forward. As shown in FIG. 7, the first anchor 27 (the first connection member) is pushed out to the abdominal cavity 53. When the needle 14 is pulled out from the tissue, the anchor 27 is placed in the abdominal cavity 53. The suture thread 25 penetrates the tissue in the wall of the stomach 43. Next, the needle 14 is thrust again in the same direction (direction toward the abdominal cavity 43 from the inside of the stomach 43) at an approximately symmetrical position across the perforation 52 with respect to the position at which the needle 14 is thrust to place the first anchor 27. When the tip of the needle 14 penetrates the tissue and projects to the abdominal cavity 53 side, the second anchor 27 the second connection member) is pushed out. As shown in FIG. 8, the second anchor 27 (the second connection member) is placed at an approximately symmetrical position across the perforation 52 with respect to the position at which the first anchor 27 is placed.

Figure 9:
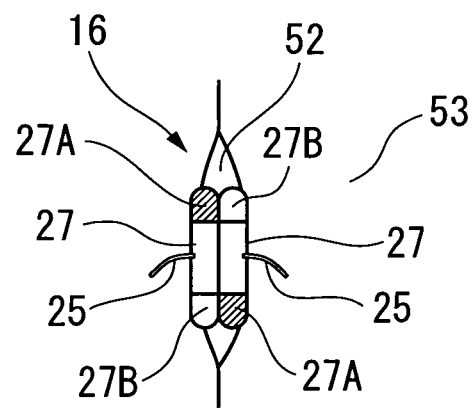
FIG. 9 is a view in which anchors are made to attach to each other.
Figure 10:
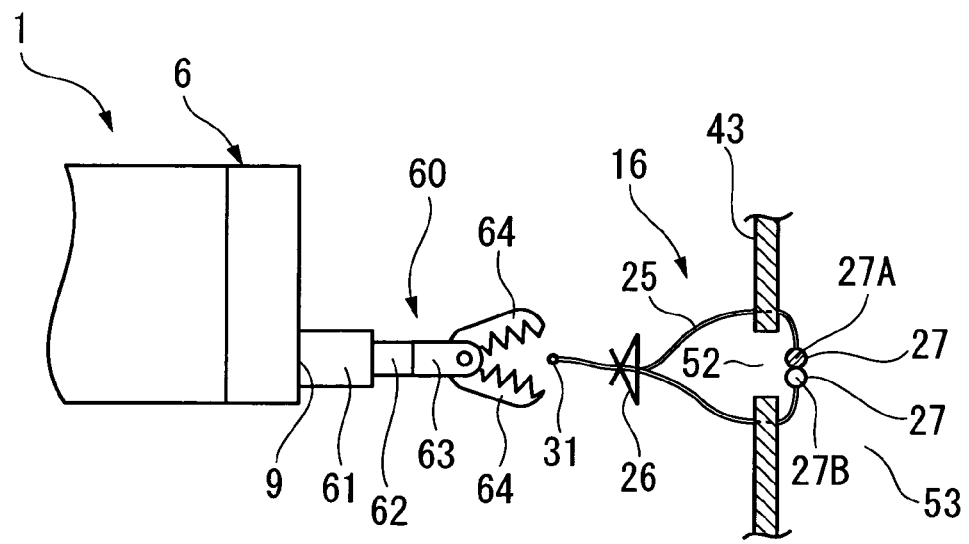
FIG. 10 is a view in which a suture thread of a suture instrument is gripped by a forceps.

Since the two anchors 27 have the end portions 27A and 27B which are polarized, one end portion 27A of the first anchor 27 and the other end portion 27B of the second anchor 27 attract each other. In the same way, one end portion 27B of the first anchor 27 and the other end portion 27A of the second anchor 27 attract each other. Accordingly, as shown in FIG. 9, the two anchors 27 attach to each other before closing the perforation 52. Since the thrust positions are near, the two anchors 27 adhere parallel to each other. By attachment of the two anchors 27, both end portions of the suture thread 25 are connected via these anchors 27.

After the suture instrument 16 is mounted on the wall so as to cross the perforation 52, the suture instrument 16 is tightened up. In order to tighten up the suture instrument 16, a forceps 62 shown in FIG. 10, for example, is used. The forceps 60 includes an outer sheath 61 having an external diameter larger than the anchor 27 and an inner sheath 62 passing through the inside of the outer sheath 61 so as to be able to freely move forward or backward. At the tip of the inner sheath 62, a supporting member 63 is provided, and a pair of grip segments 64 are supported on the supporting member 63 so as to be able to freely open or close.

Figure 11:
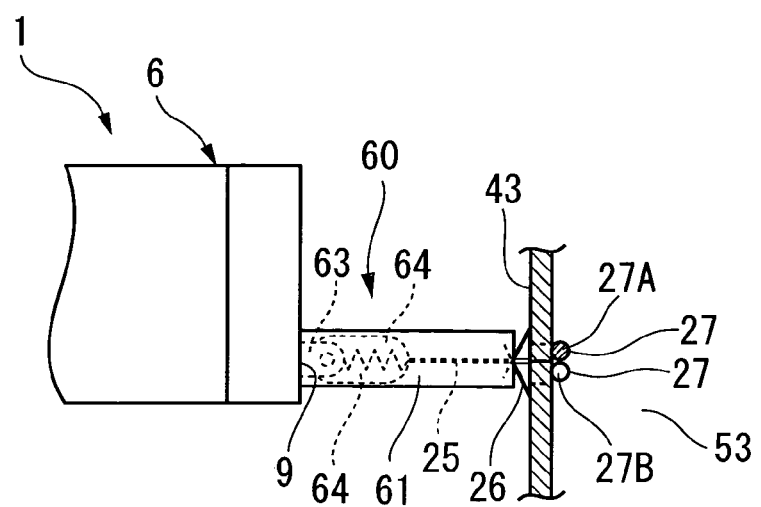
FIG. 11 is a view in which a suture instrument is tightened up by an outer sheath of a forceps.

After the knot 31 of the suture thread 25 of the suture instrument 16 is gripped by the grip segments 64, the outer sheath 61 is moved forward to press the tip of the outer sheath 61 against the stopper 26. As shown in FIG. 11, when the outer sheath 61 is moved further forward, the stopper 26 is pushed into the wall of the stomach 43. Since the stopper 26 is constructed to be able to move in this direction, the stopper 26 moves toward the wall. Since the position of the pair of the grip segments 64 does not change, the stopper 26 moves relatively forward with respect to the suture thread 25. As a result, the distance between the stopper 26 and the anchor 27 decreases, and the suture thread 25 is gathered. This pulls together the tissue around the perforation 52 as shown in FIGS. 12 and 13, and the perforation 52 is sutured by the suture thread 25.

After the perforation 52 is sutured by the suture instrument 16, the outer sheath 61 is moved backward, and then the grip segments 64 are opened to release the suture thread 25. Although the tip of the stopper 26 can move in a direction in which the tissue is tightened up by the suture thread 25, it acts to tighten up the suture thread 25 in a direction for loosening the suture thread 25. As a result, the suture thread 25 is not loosened, even if the suture instrument 16 is placed inside of the stomach 43.

Figure 12:
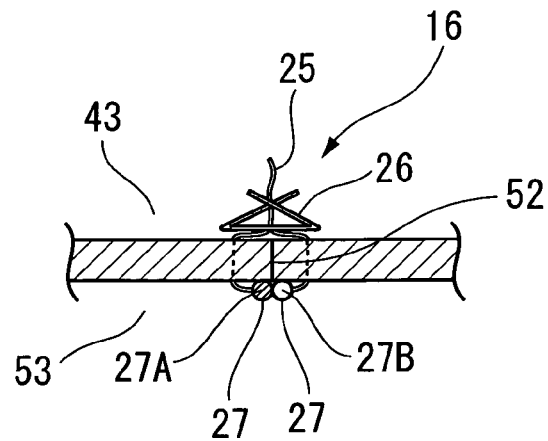
FIG. 12 is a view showing a suture instrument placed inside of the body.
Figure 13:
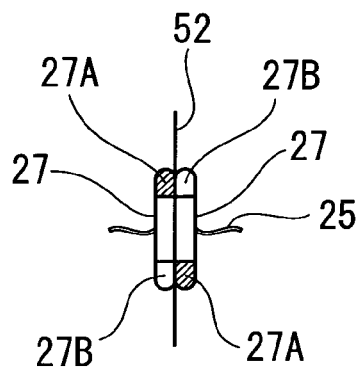
FIG. 13 is a view indicating the suture instrument of FIG. 12 as viewed from an abdominal cavity side.
Figure 14:
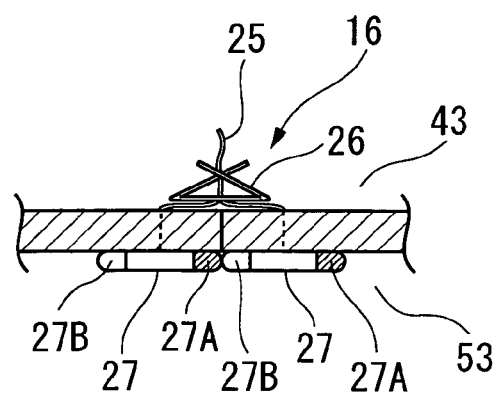
FIG. 14 is a view in which anchors are serially engaged.

As shown in FIG. 12, when the two anchors 27 attach parallel to each other, the tissue around the perforation 52 is collapsed, and the diameter of a loop of the suture thread 25 decreases. On the contrary, as shown in FIG. 14, when one end portion 27A of the first anchor 27 and the other end portion 27B of the second anchor 27 serially and attach to each other, the distance between the suture thread 25 penetrating the tissue increases. The diameter of the loop of the suture thread 25 formed via the anchor 27 increases.

In this embodiment, since a pair of the anchors 27 of the suture instrument 16 are polarized so as to pull together, the anchors 27 approach each other, and attach to each other when suturing the perforation 52. Since anchors of a suture instrument of the prior art are completely independent and attitude or position thereof cannot be controlled, the tissue around the perforation is unevenly pulled and tends to leave a gap. According to this embodiment, since the anchors 27 attach to each other, the unevenness of the tissue is prevented and the tissue around the perforation formed in the stomach 43 can close neatly. Thus, the perforation 52 is properly closed. When the anchors 27 attach parallel to each other, the attached area is large, and thereby a high engagement strength can be achieved. Moreover, since the anchors 27 are parallel to a line of closure formed due to the close contact with the inner edges of the perforation 52, the perforation 52 can be more properly closed.

Since the suture thread 25 forms a closed loop via the anchors 27 that attach to each other due to a magnetic force, it is possible to bring the inside and the outside of both sides of the tissue across the perforation 52 closely. Accordingly, as in the case of surgical suturing, suturing can be properly carried out. The diameter of the loop of the suture thread 25 can be controlled in accordance with a way of attaching the anchors 27. When the diameter of the loop is desired to be enlarged, the anchors 27 may be attached parallel to each other. When the diameter of the loop of the suture thread 25 is desired to be diminished, the anchors 27 may be closely and linearly attached to each other.

Figure 15:
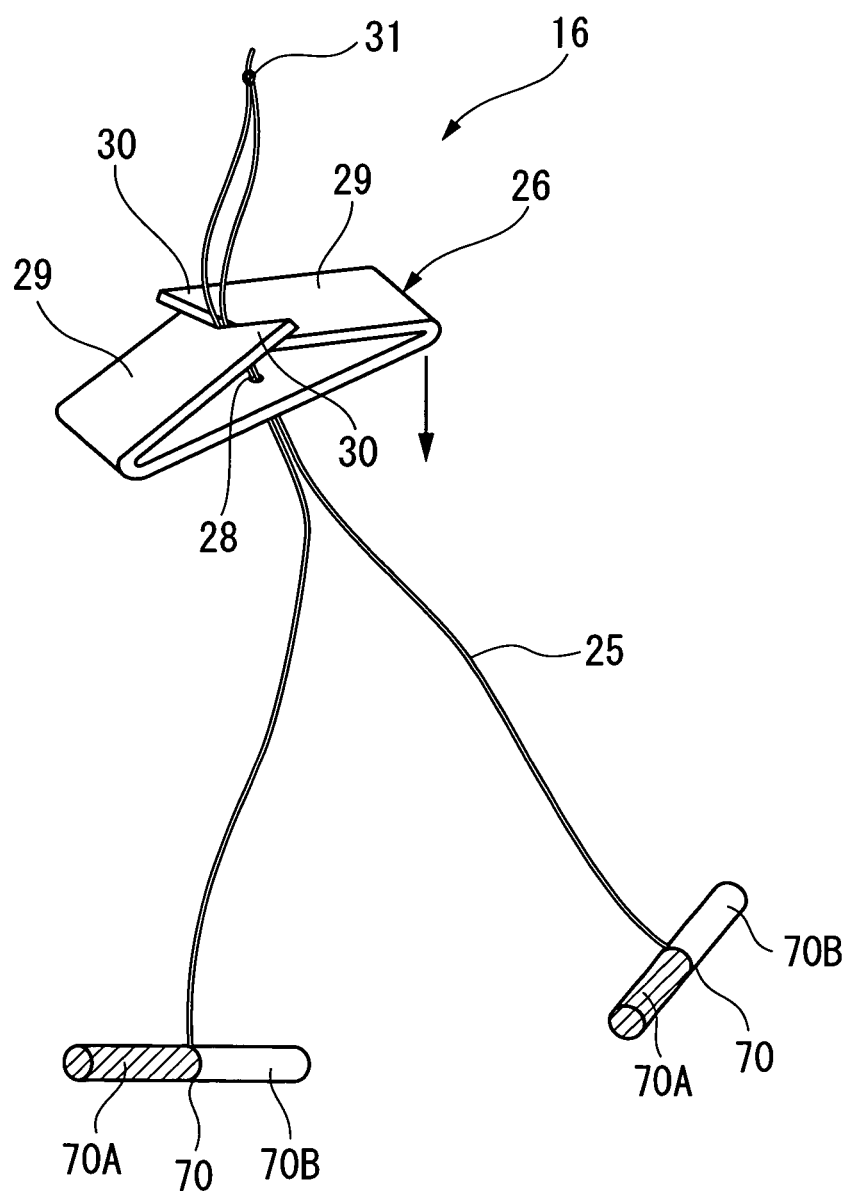
FIG. 15 is a view showing another embodiment of a suture instrument.
Figure 16:
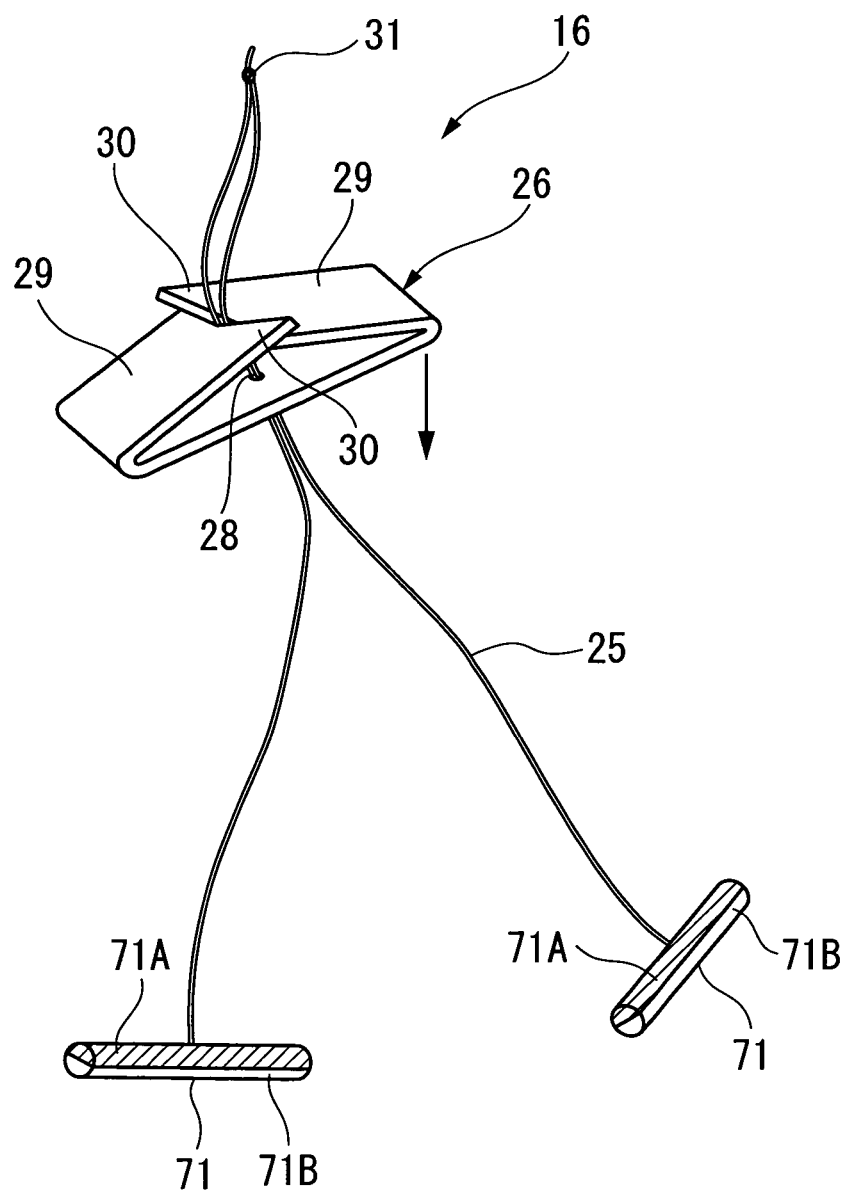
FIG. 16 is a view showing another embodiment of a suture instrument.
Figure 17:
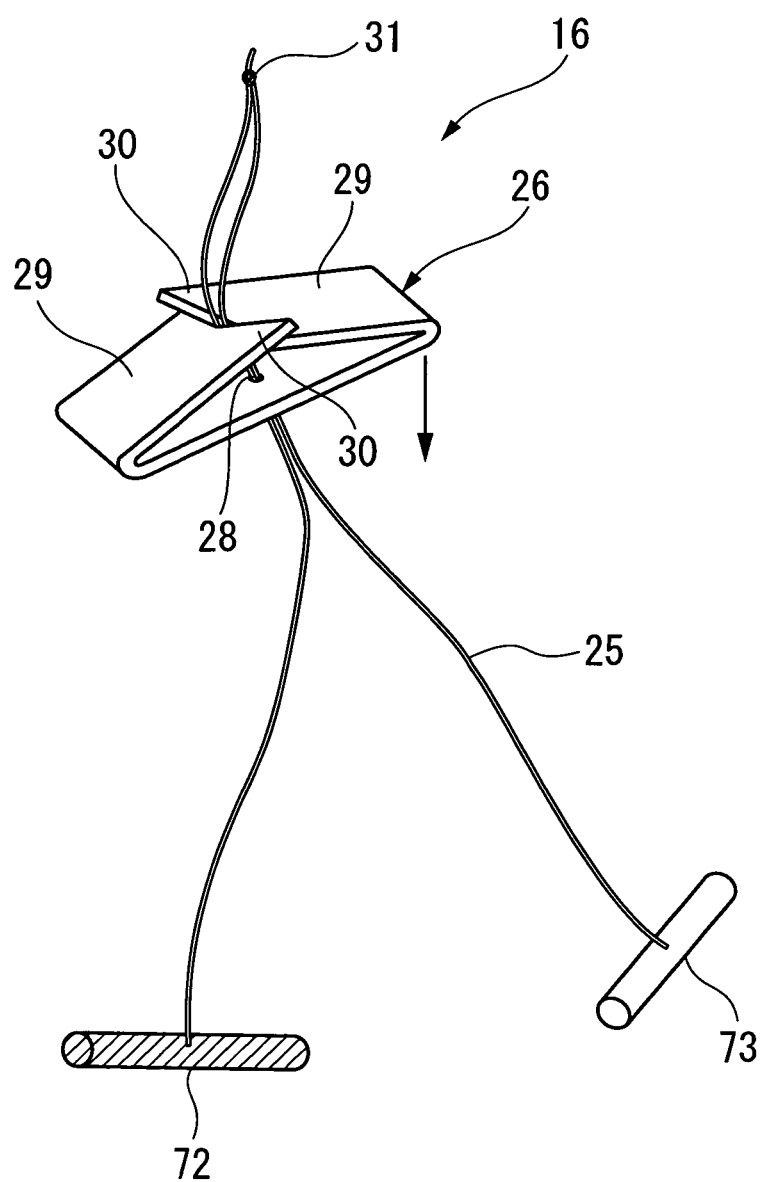
FIG. 17 is a view showing another embodiment of a suture instrument.

Another aspect of the anchor 27 is shown in FIGS. 15 to 17.

Anchors 70 as shown in FIG. 15 are connection members respectively provided at the first and the second end portions of the suture thread 25 and divided in two perpendicularly in a longitudinal direction. One portion 70A of the connection member divided in two becomes a south pole and the other portion 70B becomes a north pole. Since the attached area due to a magnetic force is large, it becomes easy for the anchors to attach to each other.

The anchors 71 as shown in FIG. 16 are connection members respectively provided at the first and the second end portions of the suture thread 25 and divided in two parallel to a longitudinal direction. One portion 71A of the connection member divided in two becomes a south pole and the other portion 71B becomes a north pole.

As shown in FIG. 17, a first anchor 72 is a first connection member provided at the first end portion of the suture thread 25 and produced from a magnet. A second anchor 73 is a second connection member provided at the second end portion of the suture thread 25 and produced from a ferromagnet. As the ferromagnet, pure iron, Permalloy, or the like is used. The anchor 73 attaches to the anchor 72 due to the magnetic force of the anchor 72, and both end portions of the suture thread 25 are connected via these anchors 72 and 73. When only the anchor 72 is a magnet, the same effect as described above can be achieved.

These anchors 27, 70, 71, 72, and 73 may have a cross section of which the shape is a circle or an oval, or a cross section of which the shape is a polygon such as a tetragon.

(Second Embodiment)

In this embodiment, the same endoscope 1 and suture unit 11 as in the first embodiment are used. Descriptions that overlap with the first embodiment will be omitted.

Figure 18:
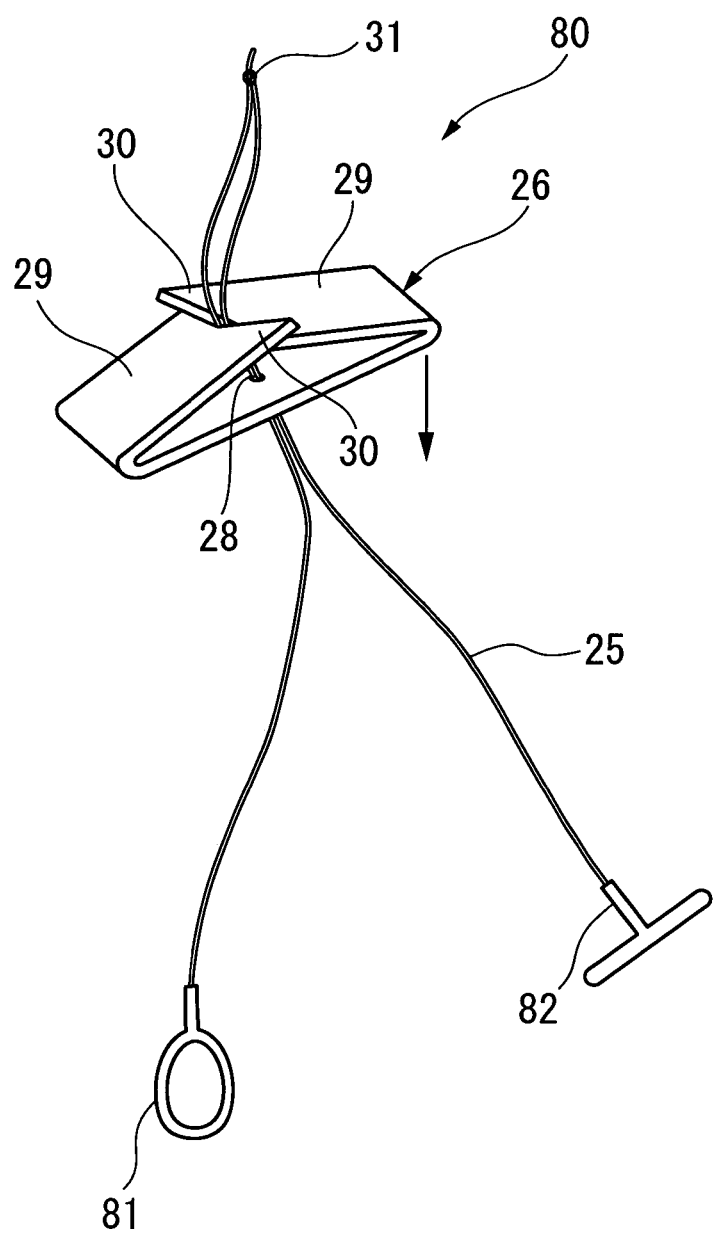
FIG. 18 is a view showing another embodiment of a suture instrument.

As shown in FIG. 18, a suture instrument 80 is equipped with a ring 81 at the first end portion of the suture thread 25. The ring 81 is a first connection member having a hole. At the second end portion of the suture thread 25, a tag 82 that is a second connection member is provided. The thickness of the tag 82 is of a size which allows it to be inserted into the inside of the ring 81. The length of the tag 82 is larger than the external diameter of the ring 81. The ring 81 and the tag 82 can be contained inside of the needle 14. For this reason, the ring 81 and the tag 82 are made from a material having flexibility and are held in the needle 14 in a folded form. The ring 81 and the tag 82 may be produced so as to be in a size smaller than the inner diameter of the needle 14.

A suturing method of this embodiment will be explained.

Figure 19:
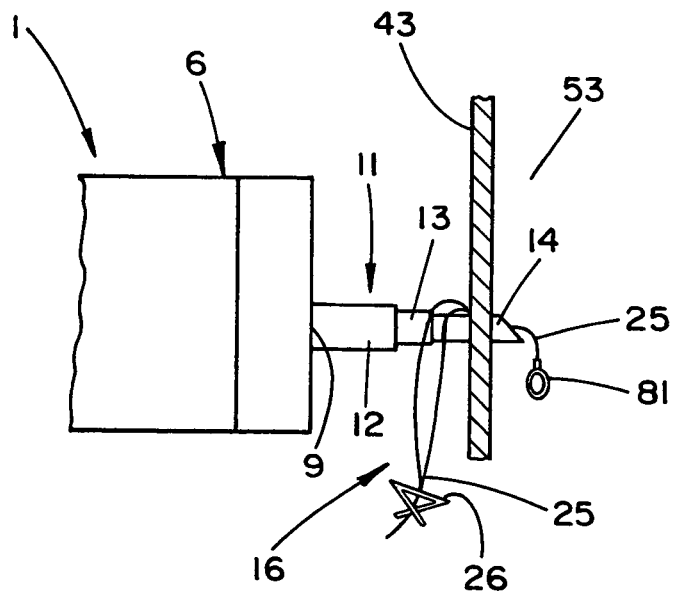
FIG. 19 is a view showing a step of thrusting a needle to extrude an anchor into an abdominal cavity side.

As shown in FIG. 5, the endoscope I is directed to the stomach 43. As shown in FIG. 6, the endoscope insertion part 6 enters the abdominal cavity 53 through the perforation 52. By using the forceps 54 passed through the endoscope insertion part 6, the treatment is carried out in the abdominal cavity 53. When the perforation 52 is sutured, the suture unit 11 is used. As shown in FIG. 19, after the needle 14 of the suture unit 11 penetrates the tissue around the perforation 52 from the inside of the stomach 43 toward the abdominal cavity 53, the pusher 20 is moved forward, and the ring 81 is pushed out from the needle 14. When the ring 82 is pushed out, the needle 14 is drawn back to be pulled out from the tissue. Moreover, the needle 14 penetrates at an approximately symmetrical position across the perforation 52 in the same direction as for placing the ring 81, that is, from the inside of the stomach 43 toward the abdominal cavity 53. The pusher 20 is moved further forward. From the needle 14, the tag 82 is pushed out to the abdominal cavity 53 side. When the tag 82 is pushed out, the needle 14 is pulled out from the wall.

Figure 20:
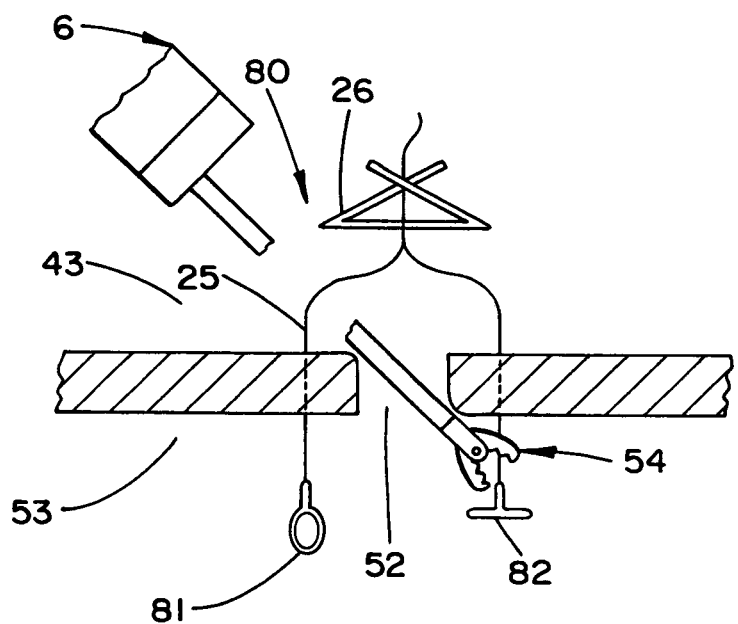
FIG. 20 is a view showing a step of engaging anchors with each other.
Figure 21:
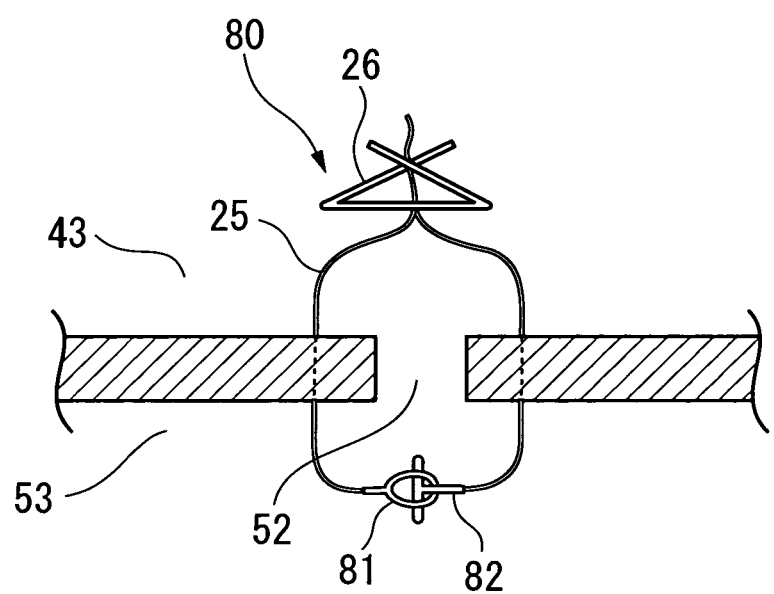
FIG. 21 is a view in which anchors are engaged with each other.

As shown in FIG. 20, the forceps 54 is passed through the channel 9 of the endoscope 1. The forceps 54 is directed through the perforation 52 to the abdominal cavity 53, and grips the tag 82 in the abdominal cavity 53. This tag 82 is inserted inside of the ring 81. As shown in FIG. 21, the ring 81 is engaged with the tag 82, and both end portions of the suture thread 25 are connected to each other via the ring 81 and the tag 82.

After the forceps 54 is pulled back from the perforation 52 to the stomach 43, the suture instrument 80 is tightened up. The tightening method is the same as in the first embodiment. A loop of the suture thread 25 is formed to close the perforation 52.

According to this embodiment, since the ring 81 and the tag 82 are respectively provided at the end portion of the suture thread 25, the loop of the suture thread 25 can be properly formed by engaging the ring 81 with the tag 82, and thereby the perforation can be properly sutured.

Figure 22:
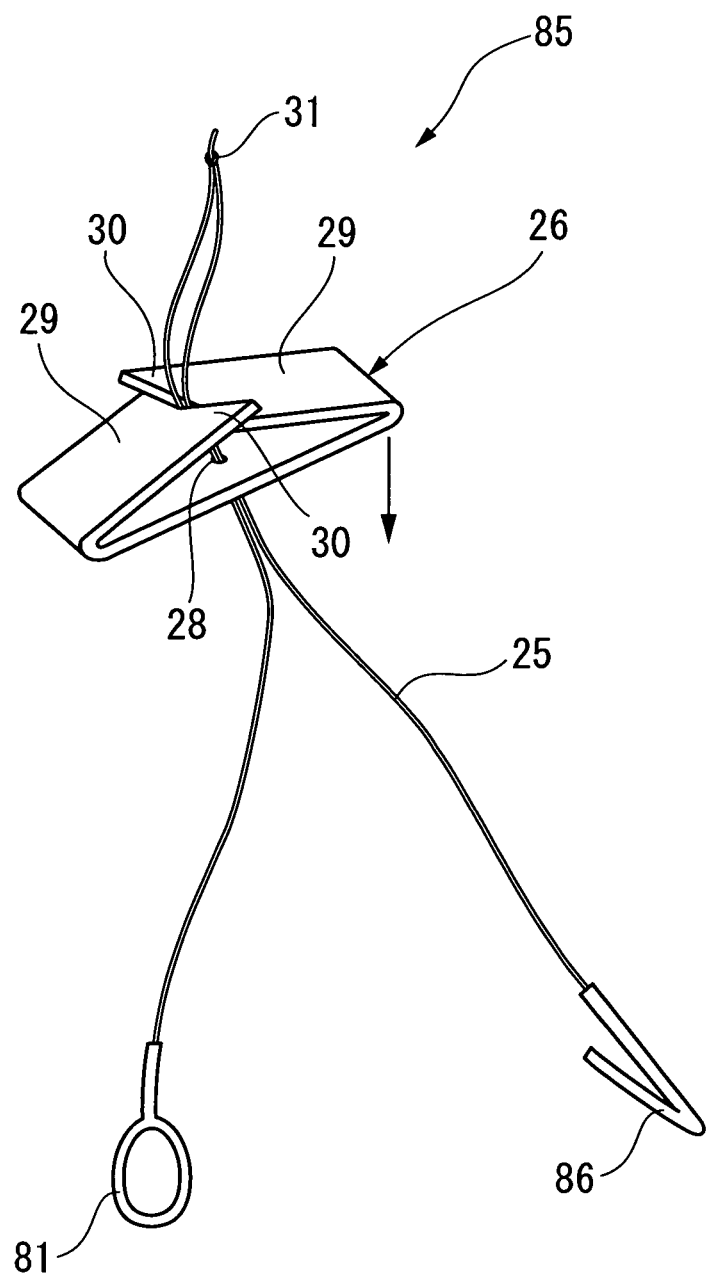
FIG. 22 is a view showing another embodiment of a suture instrument.
Figure 23:
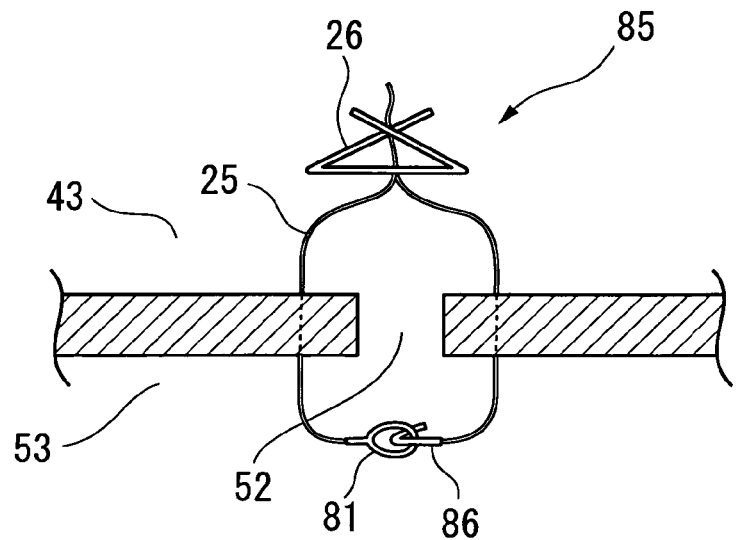
FIG. 23 is a view in which anchors are engaged with each other.

Next, another embodiment of the suture instrument is shown in FIG. 22. A suture instrument 85 is equipped with the ring 81 at the first end portion of the suture thread 25. At the second end portion of the suture thread 25, a hook 86 is provided as a second connection member. The hook 86 is thinner than the internal diameter of the ring 81 and the tip portion thereof is folded back so as to be able to be engaged with the ring 81. As shown in FIG. 23, the ring 81 and the hook 86 of the suture instrument 85 are engaged with each other at the abdominal cavity 53 side. By the ring 81 and the hook 86, the end portions of the suture thread 25 are connected with each other to form a loop. By this suture instrument 85, the perforation 52 can be closed in the same manner as with the suture instrument 80 shown in FIG. 21.

Moreover, this invention can be widely applied without being limited to the above-mentioned embodiments.

The form of the end portion of the suture thread 25 is not limited to a magnet, ring, tag, hook, or the like. After bundling the end portions of the suture thread 25, the end portions may be engaged with each other by a treatment tool such as a clip, high-frequency forceps, or the like, followed by tightening up the suture thread 25. The suture thread 25 may be tightened up after the end portions of the suture thread 25 are adhered to each other by using an adhesive agent.

The anchors 27 of the first embodiment may be gripped by a treatment tool to force them to attach to each other, followed by tightening up the suture thread 25.

Figure 24:
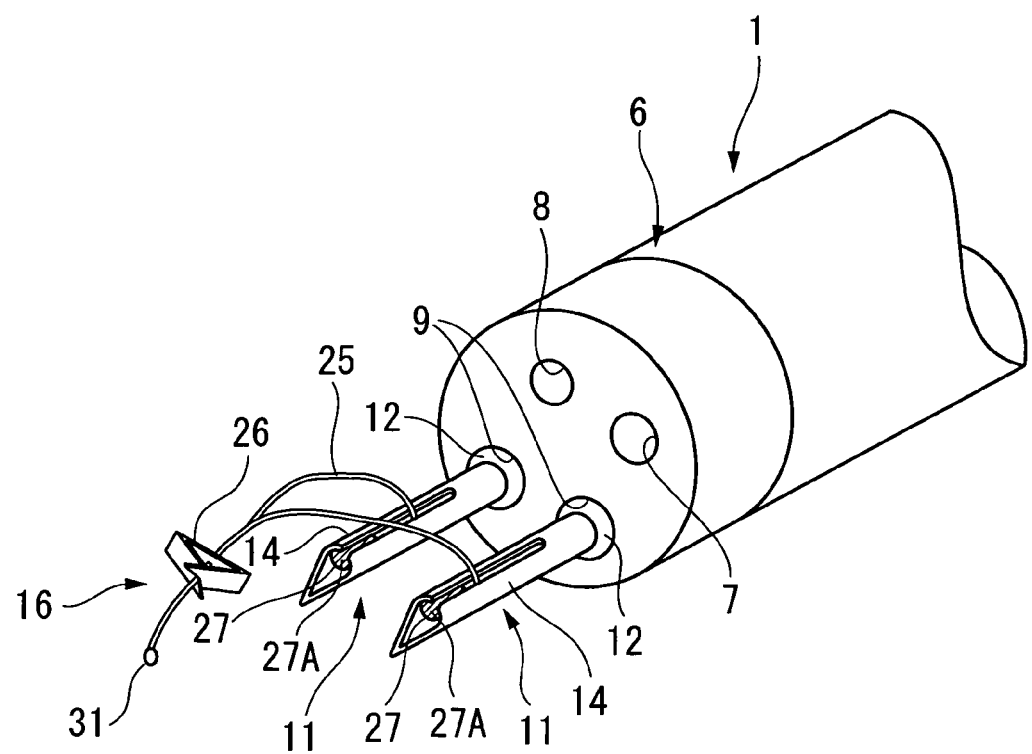
FIG. 24 is a view in which two suture units are passed through an endoscope.

As shown in FIG. 24, when the endoscope insertion part 6 has two channels 9, the suture units 11 may be passed individually through respective channels 9. In this case, the anchors 27 of the suture instrument 16 are individually held in the needle 14 of the respective suture unit 11. The same can be applied to other types of the anchor.

What is claimed is:

1. A method for suturing a perforation formed in a hollow organ by a suture thread, comprising the steps of:
    causing a first end portion and a second end portion of the suture thread to penetrate through tissues on both sides of the perforation in a same direction as each other, each of the first end portion and the second end portion including an anchor, the anchor having an outer side surface which has a longitudinal shape and connects a distal end and a proximal end of the anchor, each of the first end portion and the second end portion being connected to the outer side surface and being formed in a T-shape;
    forming a loop of the suture thread by connecting the anchors provided at the first end and the second end portions of the suture thread to each other outside of the tissues such that the outer side surfaces of the anchors are parallel to each other after the first end and the second end portions of the suture thread penetrate through the tissues on the both sides of the perforation, wherein a side opposite to the outer side surface connected to the first end portion and a side opposite to the outer side surface connected to the second end portion are connected to each other, the first end portion and the second end portion being disposed so as to face each other, the suture thread extending from each of the anchors toward an outside of the perforation;
    displacing a stopper, which the suture thread penetrates through, relative to the suture thread so as to be close to a side of the first and second end portions of the suture thread after connecting the first end and the second end portions of the suture thread to each other;
    moving the tissues on the both sides of the perforation in directions of being close to each other and closing the perforation, by pulling the suture thread so as to be close to an opposite side of the side of the end portions such that a diameter of the loop decreases; and
    maintaining a tensional force of the suture thread by the stopper holding the suture thread.

2. The method according to claim 1, wherein in the step of forming the loop of the suture thread by connecting the first end and the second end portions of the suture thread to each other, the anchors provided at each of the first end and the second end portions of the suture thread are attached to each other, and the first end and the second end portions of the suture thread are connected to each other via the anchors.

3. The method according to claim 1, wherein in the step of maintaining the tensional force of the suture thread by the stopper holding the suture thread, end portions of the stopper automatically close on the suture thread.

4. The method according to claim 1, wherein in the step of maintaining the tensional force of the suture thread by the stopper holding the suture thread, the stopper holding the suture thread has a hole through which the suture thread penetrates and has a holding part which holds the suture thread.

5. The method according to claim 1, wherein in the step of forming the loop of the suture thread by connecting the first end and the second end portions of the suture thread to each other, at least one of the anchors is magnetized, and the anchors are connecting by a magnetic force.

6. The method according to claim 1, wherein in the step of causing the first end portion and the second end portion of the suture thread to penetrate through the tissues, the first end portion and the second end portion are respectively connected to a center in a longitudinal direction of each of the anchors.

7. The method according to claim 5, wherein in the step of forming the loop of the suture thread, each of the anchors has magnetic poles opposite each other at a distal side and a proximal side in a longitudinal direction thereof, and the anchors are fixed to each other so as to be parallel to each other by connecting each of the magnetic poles of a first of the anchors and each of the magnetic poles of a second of the anchors which has a magnetic polarity opposite to each of the magnetic poles of the first of the anchors.

* * * * *